United States Patent
Kuhn

(10) Patent No.: US 6,489,520 B2
(45) Date of Patent: Dec. 3, 2002

(54) PROCESS FOR THE PREPARATION OF CIS-2-TERTIARY-BUTYLCYCLOHEXANOL BY CATALYTIC HYDROGENATION OF 2-TERTIARY-BUTYLPHENOL

(75) Inventor: Walter Kuhn, Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 10/013,206

(22) Filed: Dec. 7, 2001

(65) Prior Publication Data

US 2002/0087034 A1 Jul. 4, 2002

(30) Foreign Application Priority Data

Dec. 11, 2000 (DE) ......................................... 100 61 540

(51) Int. Cl.$^7$ ............................................... C07C 35/08
(52) U.S. Cl. .......................................... 568/834; 512/23
(58) Field of Search ............................. 568/834; 512/23

(56) References Cited

U.S. PATENT DOCUMENTS

| | | | |
|---|---|---|---|
| 4,053,524 A | * 10/1977 | Stapp | |
| 4,343,955 A | 8/1982 | Oshima et al. | ............. 568/834 |
| 4,551,564 A | 11/1985 | Otte et al. | ................... 568/834 |
| 4,751,214 A | * 6/1988 | Gramlich | |
| 5,977,402 A | * 11/1999 | Sekiguchi | |

FOREIGN PATENT DOCUMENTS

| | | |
|---|---|---|
| JP | 49-45036 | 4/1974 |
| JP | 59-65031 | 4/1984 |

OTHER PUBLICATIONS

Perfume & Flavour Chemicals, No. 438, Montclair, N.J. (month unavailable) 1969 ortho–tertiary–Butyl Cyclohexyl Acetate.

H. L. Goering, et al, "The synthesis, assignment of configuration and dehydration of cis– and trans– 2–t–butylcyclohexanol", Journal of the American Chemical Society, Bd. 78, Nr. 19, Oct. 5, 1956, 4926–4931, XP002196172, American Chemical Society, Washington, DC, US, ISSN 0002–7863.

B. Silberova, et al, "Hydrogenation of 2–tert–butylphenol over Ni catalyst", Reaction Kinetics and Catalysis Letters, Bd. 67, Nr. 1, (month unavailable) 1999, pp. 29–33 XP001073518, Elsevier Science Publishers, Amsterdam, NL ISSN: 0133–1736.

* cited by examiner

Primary Examiner—Michael L. Shippen
(74) Attorney, Agent, or Firm—Joseph C. Gil; Noland J. Cheung

(57) ABSTRACT

The present invention relates to a process for the preparation of cis-2-tertiary-butylcyclohexanol, where 2-tertiary-butylphenol is hydrogenated in the presence of a nickel/iron catalyst mixture and 2-tertiary-butylcyclohexyl acetate.

17 Claims, No Drawings

PROCESS FOR THE PREPARATION OF CIS-2-TERTIARY-BUTYLCYCLOHEXANOL BY CATALYTIC HYDROGENATION OF 2-TERTIARY-BUTYLPHENOL

FIELD OF THE INVENTION

The invention relates to a process for the preparation of cis-2-tertiary-butylcyclohexanol from 2-tertiary-butylphenol, the cis-isomer being formed under the hydrogenation conditions.

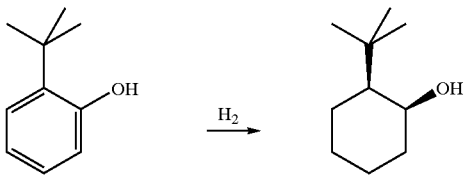

BACKGROUND OF THE INVENTION 2-tertiary-butylcyclohexanol, which can arise in the form of the cis and trans stereoisomers, is a valuable intermediate for the preparation of the fragrance 2-tertiary-butylcyclohexyl acetate. In the industrial production of 2-tertiary-butylcyclohexanol, it is desired to obtain large proportions of the cis isomer in order then, by means of transesterification, to obtain cis-2-tertiary-butylcyclohexyl acetate, which is valuable from a perfumery viewpoint and is known under the name Argrumex HC.

For the hydrogenation of 2-tertiary-butylphenol to 2-tertiary-butylcyclohexanol, noble metal catalysts, such as metallic rhodium, rhodium/platinum and rhodium/ruthenium alloys, are known, which are deposited on catalyst supports (JP-A 42-13 938). A disadvantage of the hydrogenation in the presence of a rhodium catalyst is, as well as the high cost of the catalyst, the only low stereoselectivity with regard to the cis-isomer and the decrease in the activity of the catalyst at relatively high temperatures. In addition, tertiary-butylbenzene forms in the rhodium-catalyzed hydrogenation.

DE A 3401343 describes the hydrogenation of 2-tertiary-butylphenol to 2-tertiary-butylcyclohexanol in the presence of palladium and ruthenium, the process being carried out in two stages at hydrogen pressures above 200 bar and temperatures of 70°–200° C. In the first stage, a palladium catalyst is used, and in the second stage, a ruthenium catalyst is used. The cis/trans ratio here is up to 90/10.

JP A 59/065031 describes the hydrogenation of 2-tertiary-butylphenol to 2-tertiary-butylcyclohexanol with Raney cobalt catalysis at 50 bar and 150° C., the cis:trans isomer mixture being formed in the ratio 94:6.

DE A 2909663 describes the hydrogenation of 2-tertiary-butylphenol to 2-tertiary-butylcyclohexanol with ruthenium catalysis at 40 bar and 100° C., the cis:trans isomer mixture being formed in the ratio 92.5:7.5.

JP A 49/045037 describes the hydrogenation of 2-tertiary-butylphenol to 2-tertiary-butylcyclohexanol with Raney nickel catalysis at 80 bar and 85° C. The Raney nickel catalyst is treated prior to use with aqueous sodium boronate solution. Using this catalyst treated in this way, the cis:trans isomer mixture is formed in the ratio 92:8. Without treatment of the Raney nickel catalyst, the cis:trans isomer mixture forms in the ratio 80:20.

A disadvantage of the described prior art is that the service life of the catalyst and the proportion of the cis isomer are inadequate.

SUMMARY OF THE INVENTION

Accordingly, it is an object of the present invention to provide a process which produces 2-tertiary-butylcyclohexanol with a high cis isomer content at low cost and guarantees a catalyst service life which is longer than in the prior art.

A process for the preparation of cis-2-tertiary-butylcyclohexanol has been found which is characterized in that 2-tertiary-butylphenol is hydrogenated in the presence of a nickel/iron catalyst mixture and 2-tertiary-butylcyclohexyl acetate.

DETAILED DESCRIPTION OF THE INVENTION

According to the present invention, preference is given to the use of Raney nickel/iron catalysts. The use of these catalysts in combination with 2-tertiary-butyl-cyclohexyl acetate leads to a 2-tertiary-butylcyclohexanol with a cis/trans isomer mixture of up to 95:5.

By adding 2-tertiary-butylcyclohexyl acetate, the service life of the catalyst can be considerably prolonged. It has been found that the Raney catalyst can be used more than 10 times, if 2-tertiary-butylcyclohexyl acetate is added without the cis:trans ratio falling below 90:10.

Comparative experiments have, on the other hand, shown that without the addition of 2-tertiary-butylcyclohexyl acetate in the hydrogenation, the cis:trans ratio is only 92:8. If the catalyst is used again, the cis:trans ratio decreases even more. When the catalyst is reused for only the third time without the addition of 2-tertiary-butylcyclohexyl acetate, the ratio is only 90:10.

For the process according to the present invention, the catalyst can be used in the dry or moist state.

For the process according to the present invention, in the dry catalyst, the amount of iron is 2–40% by weight, preferably 10–20% by weight; the content of nickel is 60–95% by weight, preferably 70–85% by weight, the content of aluminium is 1–20% by weight, preferably 3–10% by weight.

For the process according to the invention, the weight ratio of the catalyst used to 2-tertiary-butylphenol is (0.0001 to 0.1): 1, preferably (0.01 to 0.03): 1.

The weight ratio of the feed materials 2-tertiary-butylphenol and 2-tertiary-butylcyclohexyl acetate can be 100–0.2:1, preferably 7–9:1.

The reaction temperature for the process according to the invention is 50 to 200° C., preferably 90 to 130° C.

The hydrogen pressure is 1 to 100 bar, preferably 10 to 20 bar.

The reaction time is 2 to 100 hours, preferably 5 to 20 hours.

The process according to the present invention is generally carried out as follows:

A pressurized container fitted with stirrer is charged with 2-tertiary-butylphenol, 2-tertiary-butylcyclohexyl acetate and the catalyst. Hydrogenation is carried out at the chosen reaction temperature and hydrogen pressure. The resulting cis-2-tertiary-butylcyclohexanol is obtained following removal of the catalyst by filtration, decantation or centrifugation.

The resulting crude mixture can be reacted without further pretreatment with acetic anhydride to give the target product cis-2-tertiary-butylcyclohexyl acetate. Cis-2-tertiary-butylcyclohexyl acetate is a fragrance with woody-fruity properties (S. Steffen Arctander, Perfume and Flavour Chemicals, No. 438, Montclair, N.J., 1969).

EXAMPLES

Example 1

A stirred autoclave fitted with gas dispersion stirrer is charged with 520 g of 2-tertiary-butylphenol, 80 g of 2-tertiary-butylcyclohexyl acetate and 17 g of Raney nickel/iron (water content 44%, nickel content 45%, iron content 8%, aluminium content 3%). Hydrogenation is carried out for 10 hours at 130° C. and then for 3 h at 100° C. The hydrogen pressure is 20 bar. Following filtration, 605 g of a crude mixture are obtained.

According to gas chromatographic analysis, the crude mixture has the following composition:

84.1% of cis-2-tertiary-butylcyclohexanol, 4.6% of trans-2-tertiary-butylcyclohexanol, 10.5% of cis-2-tertiary-butylcyclohexyl acetate, 0.5% of trans-2-tertiary-butylcyclohexyl acetate and 0.2% of 2-tertiary-butylcyclohexanone.

The ratio of cis:trans 2-tertiary-butylcyclohexanol is 95:5.

Examples 2–13

The following batches 2–13 proceed analogously to 1, the catalyst from the starting batch 1 being reused. The cis:trans ratio varies between 94:6 and 91:9.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of cis-2-tertiary-butylcyclohexanol, comprising the step of hydrogenating 2-tertiary-butylphenol in the presence of a nickel/iron catalyst mixture and 2-tertiary-butylcyclohexyl acetate.

2. A process according to claim 1, wherein said nickel/iron catalyst mixture is a Raney nickel/iron catalyst.

3. A process according to claim 1, wherein the catalysts are used in the dry or moist state.

4. A process according to claim 3, wherein the catalysts in the dry state have an iron content of 2–40% by weight, a nickel content of 60–95% by weight and an aluminum content of 1–20% by weight.

5. A process according to claim 4, wherein the catalysts in the dry state have an iron content of 10–20% by weight; a nickel content of 70–85% by weight and an aluminum content of 3–10% by weight.

6. A process according to claim 1, wherein the weight ratio of 2-tertiary-butylphenol to 2-tertiary-butylcyclohexyl acetate is 100:1 to 0.2:1.

7. A process according to claim 6, wherein the weight ratio of 2-tertiary-butylphenol to 2-tertiary-butylcyclohexyl acetate is 7:1 to 9:1.

8. A process according to claim 2, wherein the weight ratio of Raney catalyst to 2-tertiary-butylphenol is 0.0001:1 to 0.1:1.

9. A process according to claim 8, wherein the weight ratio of Raney catalyst to 2-tertiary-butylphenol is 0.01:1 to 0.03:1.

10. A process according to claim 1, wherein the reaction temperature is between 50 and 200° C.

11. A process according to claim 10, wherein the reaction temperature is between 90 and 130° C.

12. A process according to claim 1, wherein the hydrogen pressure is between 1 and 100 bar.

13. A process according to claim 12, wherein the hydrogen pressure is between 10 and 20 bar.

14. A process according to claim 1, wherein the reaction time is between 2 and 100 hours.

15. A process according to claim 14, wherein the reaction time is between 5 and 20 hours.

16. A process for the preparation of 2-tertiary-butylcyclohexanol according to claim 1, wherein said 2-tertiary-butylcyclohexanol has a cis:trans isomer ratio of 95:5.

17. A process for the preparation of a fragrance containing 2-tertiary-butylcyclohexyl acetate comprising the step of hydrogenating 2-tertiary-butylphenol in the presence of a nickel/iron catalyst mixture and 2-tertiary-butylcyclohexyl acetate.

* * * * *